US008906111B2

(12) United States Patent
Tei et al.

(10) Patent No.: US 8,906,111 B2
(45) Date of Patent: Dec. 9, 2014

(54) ARTIFICIAL BONE MATERIAL HAVING CONTROLLED CALCIUM ION ELUTION

(75) Inventors: Yuichi Tei, Bunkyo-Ku (JP); Nobuo Sasaki, Bunkyo-Ku (JP); Shigeki Suzuki, Bunkyo-Ku (JP)

(73) Assignees: The University of Tokyo, Tokyo (JP); Next21 K.K., Tokyo (JP)

( * ) Notice: Subject to any disclaimer, the term of this patent is extended or adjusted under 35 U.S.C. 154(b) by 476 days.

(21) Appl. No.: 13/002,148

(22) PCT Filed: Jul. 1, 2009

(86) PCT No.: PCT/JP2009/003047
§ 371 (c)(1),
(2), (4) Date: Mar. 7, 2011

(87) PCT Pub. No.: WO2010/001601
PCT Pub. Date: Jan. 7, 2010

(65) Prior Publication Data
US 2011/0183000 A1  Jul. 28, 2011

(30) Foreign Application Priority Data
Jul. 2, 2008 (JP) ................................. 2008-174025

(51) Int. Cl.
*A61L 27/00* (2006.01)
*A61L 27/50* (2006.01)
*A61L 27/12* (2006.01)

(52) U.S. Cl.
CPC ................. *A61L 27/50* (2013.01); *A61L 27/12* (2013.01); *A61L 2430/02* (2013.01)
USPC ..................... 623/23.62; 623/16.11; 424/423; 424/696

(58) Field of Classification Search
CPC ....... A61L 27/00; A61L 27/025; A61L 27/12; A61L 27/50
See application file for complete search history.

(56) References Cited

U.S. PATENT DOCUMENTS

| 6,994,726 B2* | 2/2006 | Lin et al. ..................... 623/16.11 |
| 2004/0082998 A1 | 4/2004 | Shinomiya et al. |
| 2005/0031704 A1 | 2/2005 | Ahn |
| 2010/0003301 A1* | 1/2010 | Sasaki et al. .................. 424/423 |

FOREIGN PATENT DOCUMENTS

| JP | 7-8547 A | 1/1995 |
| JP | 2001-198208 A | 7/2001 |
| JP | 2002-248119 A | 9/2002 |
| JP | 2004-261456 A | 9/2004 |
| JP | 2006-346159 A | 12/2006 |
| WO | 2005/032456 A2 | 4/2005 |
| WO | 2008/041774 A1 | 4/2008 |
| WO | 2008/065738 A1 | 6/2008 |
| WO | WO 2008/065738 * | 6/2008 .............. A61L 27/00 |

OTHER PUBLICATIONS

Detsch et al, "Formation of osteoclast-like cells on HA and TCP ceramics" Acta Biomaterialia, 2008, vol. 4, pp. 139-148.*
Malafaya et al "Bilayered chitosan-based scaffolds for osteochondral tissue engineering: Influence of hydroxyapatite on in vitro cytotoxicity and dynamic bioactivity studies in a specific double-chamber bioreactor" Acta Biomaterialia, 2009, vol. 5, pp. 644-660.*
Paul et al, "Effect of calcium, zinc and magnesium on the attachment and spreading of osteoblast like cells onto ceramic matrices" Journal of Materials Science: Materials in Medicine, 2007, vol. 18, pp. 699-703.*
International Search Report w/translation from PCT/JP2009/003047 dated Aug. 25, 2009 (4 pages).
Yuichi Tei; "3D Sekiso Zokei ni yoru Ishoku-yo Taylor Made Jinkokotsu no Kaihatsu to Oyo"; Japanese Journal of Oral and Maxillofacial Surgery; vol. 53, No. 3, pp. 212-223; 2007 (2 pages).
Tamotsu Yasue et al.; "Baiomimetic Process ni yoru Kozo Yugoka Zairyo no Sekkei to Sosei Biomineralization o Riyo shita Zairyo no Sosei 1.1 Baiomimetic Process ni yoru Zairyo no Sekkei to Sosei"; Nihon Daigaku Daigakuin Rikogaku Kenkyuka High-tech Research Center Seibi Jigyo Kenkyu Seika Hokokusho Heisei 11-15 Nendo Shiritsu Daigaku Gakujutsu Kenkyu Kodoka Suishin Jigyo; pp. 3-44; 2004 (43 pages).
espacenet English Abstract for JP 2006-346159 (1 page), Dec. 28, 2006.
espacenet English Abstract for JP 2002-248119 (1 page), Sep. 3, 2002.

* cited by examiner

Primary Examiner — Allison Fox
(74) Attorney, Agent, or Firm — Osha Liang LLP

(57) ABSTRACT

Disclosed is an artificial bone material having controlled calcium ion elution, which does not induce cytotoxicity or any inflammatory response. It is found that the elution of a calcium ion from an artificial bone material for transplantation which contains a calcium-containing substance can be prevented effectively by subjecting the carrier to a surface treatment or adding a surface-treating agent to the carrier. It is also found that the induction of cytotoxicity can be prevented and the induction of an inflammatory response can also be prevented by using the above-mentioned carrier having controlled calcium ion elution.

5 Claims, 3 Drawing Sheets

ARTIFICIAL BONE MATERIAL HAVING CONTROLLED CALCIUM ION ELUTION

TECHNICAL FIELD

The present invention relates to a medical artificial bone material having controlled calcium ion elution for implantation in the body.

BACKGROUND ART

Conventionally, calcium-based materials used as artificial bone materials have been widely used for implantation in the body for therapeutic purposes. For example, JP-A No. 2006-346159 discloses a biological tissue filling material, and describes the production of a porous biological tissue filling material from calcium phosphate.

Further, JP-A No. 2002-248119 discloses an artificial vertebral body including hydroxyapatite and collagen. WO2005/032456 discloses a prosthetic implant including calcium phosphate.

As described above, calcium-based materials are widely used as biomaterials, but they have difficulty in achieving sufficient therapeutic effects when used in treatments.

PRIOR ART DOCUMENT

Patent Document

Patent Document 1: JP-A No. 2006-346159
Patent Document 2: JP-A No. 2002-248119
Patent Document 3: WO 2005/032456

DISCLOSURE OF THE INVENTION

Problems to be Solved by the Invention

The object of the present invention is to provide an artificial bone material having controlled calcium ion elution that prevents induction of cytotoxicity and inflammatory responses.

Means for Solving the Problems

Calcium ion elution from artificial bone materials such as bone filling materials and bone fillers has been completely out of consideration in the past. The present inventors have found that in some cases, implantation of artificial bone materials inhibit cell growth. On the hypothesis that a cause of the inhibition is a trace amount of calcium ion eluting from artificial bone materials, the present inventors have carried out experiments and obtained results supporting the hypothesis. Therefore, the present invention is based on the finding that the calcium ion elution from an implantable artificial bone material including a calcium-based material can be effectively suppressed by subjecting the carrier to a surface treatment or impregnating the carrier with a surface-treating agent. The present invention is also based on the finding that use of such a carrier having controlled calcium ion elution can prevent induction of cytotoxicity and moreover, induction of inflammatory responses as well. The surface treatment can remove a calcium ion eluted from an implantable artificial bone material. In addition, the impregnation of the implantable artificial bone material with the surface-treating agent can prevent calcium ion elution from the implantable artificial bone material.

One aspect of the present invention relates to a method of producing an artificial bone material having controlled calcium ion elution. The method of production of the present invention comprises a step of washing an implantable artificial bone material including a calcium-based material. The step removes calcium ions that will leave from the surface of the artificial bone material when the material is implanted in the body, thereby allowing to produce an artificial bone material having controlled calcium ion elution that can prevent the induction of inflammatory responses and cytotoxicity induced by the calcium ions in a tissue around an implanted site of the artificial bone. For the artificial bone material having controlled calcium ion elution, the amount of calcium ions to be released in a tissue around an implanted site of the artificial bone material under implanted conditions is preferably controlled to 50% or less of the amount to that from the unwashed artificial bone material. Such prevention of calcium ion elution can prevent a situation where cell growth is inhibited by calcium ions.

In a preferred embodiment of the first aspect of the present invention, the artificial bone material is sintered. Namely, when an artificial bone material is sintered in particular, a large amount of calcium ion is eluted. The present invention thus can be effectively used for such sintered artificial bone to suppress calcium ion elution by subjecting the bone to a predetermined treatment. In the step of washing, pure water, a pH buffer solution, a chelating agent solution, a capping agent solution, or a coupling agent solution is used to wash the artificial bone material.

In the preferred embodiment of the first aspect of the present invention, the method further comprises a step of permeating the implantable artificial bone material from which calcium ions have been removed by the above washing step with a surface-treating agent. The step of permeating is carried out by applying the surface-treating agent to the implantable artificial bone material from which the calcium ions have been removed or by immersing the implantable artificial bone material in a surface-treating agent solution. The method further including this step can produce an artificial bone material having controlled calcium ion elution.

In another preferred embodiment of the first aspect of the present invention, the method of producing an artificial bone material having controlled calcium ion elution comprises a step of washing an implantable artificial bone material with a gluconic acid solution and a step of permeating the washed implantable artificial bone material with gluconic acid. As described in the Examples below, gluconic acid is capable of effectively chelating calcium ions. Washing with a gluconic acid solution thus can effectively remove calcium ions leaving from the implantable artificial bone material and attaching to the surface of the material and the like. In addition, the permeation of the washed implantable artificial bone material with gluconic acid can prevent calcium ions leaving from the artificial bone material after being implanted in the affected site. Further, it prevents induction of inflammatory responses at the implanted site.

In another preferred embodiment of the first aspect of the present invention, the method of producing an artificial bone material having controlled calcium ion elution comprises a step of permeating an implantable artificial bone material with succinic acid, a step of washing the permeated implantable artificial bone material with pure water, and a step of permeating the washed implantable artificial bone material with trehalose. Dicarboxylic acids such as succinic acid serve as an chelating compound of a calcium phosphate-based material. Succinic acid is thought to cause substitution of a phosphate ion of octacalcium phosphate (OCP) to a succinate ion when contacted with OCP (Hideki Monma and Masaru Goto, "Succinate-complexed Octacalcium Phosphate" Bull.

Chem. Soc. Jpn., 56, pp. 3843-3844 (1983)). Permeation with succinic acid thus causes substitution of a phosphate ion to a succinate ion, thereby strongly fixing a calcium ion. Accordingly, the implantable artificial bone material permeated with succinic acid is thought to prevent calcium ion elution when the material is implanted in the body. Moreover, as shown in the Examples below, an artificial bone material having controlled calcium ion elution produced through these steps could prevent calcium elution from the artificial bone material and facilitate cell growth.

A second aspect of the present invention relates to an artificial bone material having controlled calcium ion elution, including an implantable artificial bone material including a calcium-based material and a surface-treating agent applied on or absorbed into the implantable artificial bone material. The artificial bone material having controlled calcium ion elution of the present invention can prevent calcium ions eluting from the implantable artificial bone material, thereby preventing induction of inflammatory responses and cytotoxicity due to calcium ions. As described in the Examples below, the artificial bone material having controlled calcium ion elution of the present invention can effectively suppress calcium ion elution, and prevents induction of inflammatory responses at the implanted site.

In a preferred embodiment of the second aspect of the present invention, the surface-treating agent is any one or a mixture of any more than one of, an acidic solution, a chelating agent, a capping agent, and a coupling agent. Use of such surface-treating agent allows to effectively suppress calcium ion elution from the implantable artificial bone material, thereby preventing induction of inflammatory responses at the carrier implanted site. In another preferred embodiment of the second aspect of the present invention, the surface-treating agent is a chelating agent. The chelating agent is one or a mixture of more than one selected from the group consisting of gluconic acid, chain polyphosphoric acid, aspartic acid, ethylenediaminetetraacetic acid, metaphosphoric acid, citric acid, nitrilotriacetic acid, and methylglycinediacetic acid. Since the chelating agent is stabilized by reacting with calcium ion, the agent can effectively chelate calcium ions eluted from the implantable artificial bone material. As shown in the Examples below, use of a chelating agent enables to effectively prevent calcium ion elution from the carrier.

In another preferred embodiment of the second aspect of the present invention, the surface-treating agent is a capping agent. The capping agent is one or a mixture of more than one selected from the group consisting of amino acids, peptides, polysaccharides, disaccharides, lectin, proteoglycan, glycoproteins, and glycolipids. Use of such capping agent can effectively prevent calcium ion elution from the implantable artificial bone material, thereby preventing induction of inflammatory responses at the implanted site. The implantable artificial bone material thus can suitably be used for treatments.

In another preferred embodiment of the second aspect of the present invention, the surface-treating agent is trehalose. As shown in the Examples below, trehalose can prevent calcium ion elution from the implantable artificial bone material, and thus, prevents induction of cytotoxicity at the implanted site.

Another preferred embodiment of the second aspect of the present invention is a coupling agent. The coupling agent is an aluminate-based, titanol-based, or silanol-based coupling agent. The coupling agent efficiently reacts with calcium ions to suppress calcium ion elution from the implantable artificial bone material. Further, these coupling agents have good biocompatibility and are suitably used.

In another preferred embodiment of the second aspect of the present invention, the artificial bone material having controlled calcium ion elution further contains a pharmaceutical agent. Inclusion of a therapeutic/prophylactic agent for the disease site where the artificial bone material having controlled calcium ion elution of the present invention is to be applied effectively enhances therapeutic effects and hastens recovery.

The pharmaceutical agent is either or both a cell membrane protective agent and an anti-inflammatory agent. In the artificial bone material having controlled calcium ion elution of the present invention, calcium ion elution is controlled. Thus, it can prevent induction of inflammatory responses at the implanted site due to eluted calcium ions from the implantable artificial bone material. However, the implantation of the artificial bone material having controlled calcium ion elution of the present invention may apply physical stimuli to cells around the implanted site and elicit responses. The artificial bone material having controlled calcium ion elution of the present invention thus also contains either or both a cell membrane protective agent and an anti-inflammatory agent. Such agent(s) as in the present invention enables to protect cells around the implanted site from physical stimuli and to prevent cells from eliciting inflammatory responses caused by physical stimuli. Accordingly, the inclusion of either or both a cell membrane protective agent and an anti-inflammatory agent hastens recovery in prognosis after treatment.

Effects of the Invention

According to the present invention, an artificial bone material having controlled calcium ion elution that can prevent induction of cytotoxicity and inflammatory responses can be provided.

BRIEF DESCRIPTION OF THE DRAWINGS

FIG. 3 is a set of graphs, in place of a set of drawings, showing gluconic acid preventing induction of inflammatory responses by calcium ion.

BEST MODE FOR CARRYING OUT THE INVENTION

Figure 1:
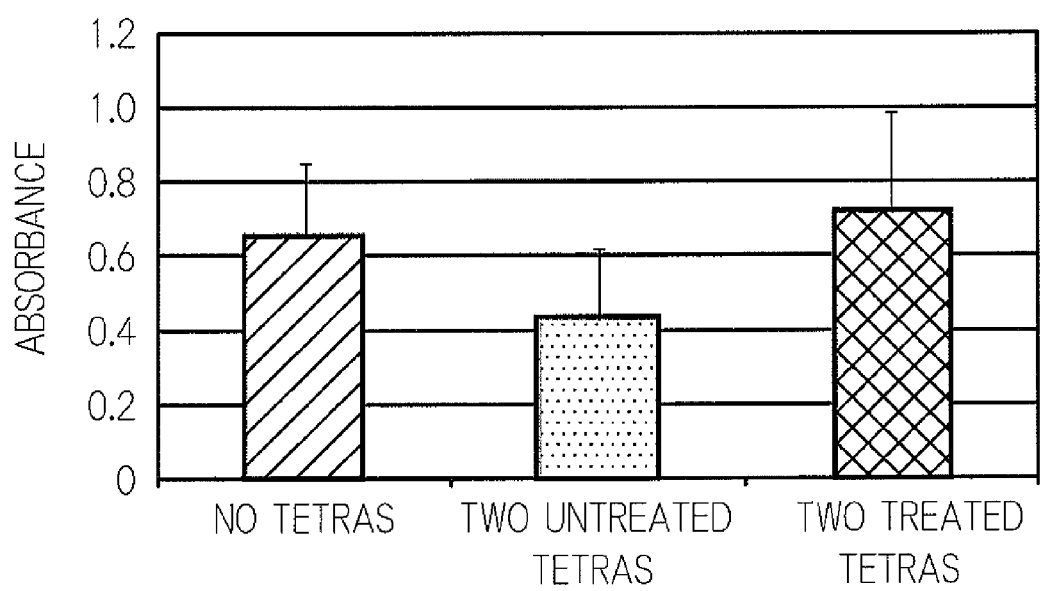
FIG. 1 is a graph, in place of a drawing, showing the affect of calcium ion elution from the carrier on cell growth.

In the present invention, the artificial bone material is essentially washed to remove Ca ions that would leave from the surface of the material. Pure water, a pH buffer solution, a salt solution, a chelating solution and the like are used for washing. By washing, induction of inflammatory responses and cytotoxicity due to the calcium ions can be prevented in a tissue adjacent to the implantable artificial bone material. A common artificial bone is sintered in order to increase hardness. The temperature of sintering is 800° C. for βTCP, and 1100° C. for αTCP. Through sintering at this temperature, contaminated pyrogens and organic matters such as endotoxin completely vaporize. An artificial bone thus produced has tendency of easily releasing calcium ion, but is usually not subjected to an after treatment for avoiding increase in risk. In the present invention, the artificial bone material is unconventionally subjected to a predetermined after treatment. Such an after treatment allows obtaining an artificial bone having controlled calcium elution from which calcium ions that would leave from the artificial bone material are removed. Further, inclusion of the surface-treating agent to the artificial bone material allows obtaining an artificial bone having controlled calcium elution in which calcium ion elution from the artificial bone material is prevented.

The present invention relates to a carrier having controlled calcium elution. The carrier having controlled calcium elution comprises an implantable artificial bone material including a calcium-based material (hereinafter, referred to as "carrier having controlled calcium elution" or "implantable artificial bone material") and a surface-treating agent applied to or absorbed into the implantable artificial bone material. The carrier having controlled calcium ion elution can prevent calcium ion elution from the implantable artificial bone material to control inflammatory responses and cytotoxicity caused by calcium ions. The carrier having controlled calcium ion elution comprises a calcium-based material, and is suitably used as a filling material for injecting into a bone defect site. Each component of the present invention will be describes below.

Artificial Bone Having Controlled Calcium Ion Elution

The artificial bone having controlled calcium ion elution is an article that can prevent calcium ion elution therefrom, has a form such as granular and blockish, and is applied to a bone defect site or a bone deformed site in the body. The artificial bone having controlled calcium ion elution has a property of gradually being substituted to a bone tissue. The artificial bone having controlled calcium ion elution contains the surface-treating agent, and thus can prevent calcium ion elution from the calcium-based material composing the artificial bone.

Method of Producing the Implantable Artificial Bone Material

The implantable artificial bone material is an article that is produced from a composition including a calcium-based material, and has a form such as granular and blockish. The form of the implantable artificial bone material is not limited to those described above, and includes, for example, a personalized implantable artificial bone material that is conformed to a shape of the applied site, a tooth root implant, and a curable artificial bone, in addition to granular and blockish implantable artificial bone material. The granular implantable artificial bone material is produced by grinding the blockish implantable artificial bone material. The blockish implantable artificial bone material includes that having multiple protrusions such as a tetrapod shape. In this case, a plurality of implantable artificial bone materials would be applied and such to an affected site. The implantable artificial bone material may also be of a designed shape considering the bone shape of a patient (personalized implantable artificial bone material) like as in an implant. Such an implantable artificial bone material is generally implanted in an affected site by surgery or the like and gradually substituted to a bone tissue.

When the implantable artificial bone material is a personalized implantable artificial bone material that is conformed to the shape of an applied site, a tooth root implant, or a curable artificial bone, the size thereof is appropriately modified according to the site to be implanted. On the other hand, when the implantable artificial bone material is used in the form of granule or block, the size of the implantable artificial bone material (a diameter of a ball enclosing the implantable artificial bone material) ranges from $1 \times 10^{-2}$ to 5 mm. Preferably, the implantable artificial bone material in the block form of the present invention includes a form having multiple protrusions that is preferably $5 \times 10^{-2}$ mm to 3 mm, more preferably $1 \times 10^{-1}$ mm to 2 mm, and even more preferably $2 \times 10^{-1}$ mm to 1.5 mm. The protrusions are designed so that they are symmetrical with respect to a line or a plane, or are spatially symmetrical. Specific examples of a preferred form include, but not limited to, a tetrapod type (a shape having a regular tetrahedron and four protrusions extending from the center of the tetrahedron to the respective corners) and regular n-hedrons (n=6, 8, 12, etc.) having n protrusions extending from the center to the respective corners. However, an implantable artificial bone material of the present invention is not limited to the above stated specific examples.

For producing the implantable artificial bone material, any known method can be used, including the method described in JP-A No. 2003-146773. An exemplary method of producing the implantable artificial bone material will be briefly described below. The exemplary method includes steps of kneading, molding, binder removal (degreasing), and sintering. A kneading step is for kneading ingredient which comprises calcium-based material and a material containing binder. A molding step is for obtaining a molded body having a predetermined shape from a kneaded material obtained in the kneading step with an injection molding machine having a mold. A binder removal (degreasing) step is for removing the binder contained in the molded body to obtain a degreased body, in which the molded body being obtained in the molding step. A sintering step is for heating and sintering the degreased body to obtain a sintered body, in which the degreased body being obtained in the binder removal step. The method may include publicly known steps such as an after treatment step for a molded body.

Calcium-Based Materials

The calcium-based material is the main component of the carrier having controlled calcium ion elution. The calcium-based material is not specifically limited as long as it is close to the bone components. Examples of such calcium-based material include calcium phosphate-based material, calcium carbonate-based material, calcium lactate, and calcium gluconate. Among them, calcium phosphate-based or calcium carbonate-based material is preferred. Specific examples of calcium phosphate-based material as powdered ingredients include one or more kinds of hydroxyapatite, carbonate apatite, fluorine apatite, chlorine apatite, β-TCP, α-TCP, calcium metaphosphate, tetra-calcium phosphate, octa-calcium phosphate, calcium hydrogen phosphate, calcium hydrogen phosphate, calcium dihydrogenphosphate, calcium pyrophosphate, and the salts thereof, and the solvates thereof. Among them, β-TCP or hydroxyapatite is preferred. Examples of calcium carbonate-based material include calcium carbonate and calcium hydrogen carbonate. Among them, calcium carbonate is preferred. Chemical compounds other than the above may be included in the calcium-based material as needed if the above chemical compounds are the main component of the calcium-based material. Use of such calcium-based material enables to produce a porous carrier having controlled calcium ion elution. If a porous carrier is applied in an affected site, cells and growth factors will enter pores to increase effects of regeneration treatment. However, when calcium ion elutes from the carrier, it elicits cytotoxicity and inflammatory responses. A smaller surface area from which calcium ions elute is accordingly preferred, and thus a non-porous carrier will result in a better prognosis. However, the carrier of the present invention can effectively prevent calcium ion elution by containing the surface-treating agent, and can be suitably applied to an affected site such as a bone defect site.

In the present invention, the ratio of the calcium-based material in the implantable artificial bone material is 70 to 95 parts by weight to 100 parts by weight of the implantable artificial bone material. The implantable artificial bone material of the present invention may further comprise sub-materials required for molding the carrier such as binders, for example, acrylic resin and the like, in addition to the calcium-based material and the surface-treating agent. Such sub-materials may be appropriately used by those skilled in the art.

Step of Washing

Calcium ions on the surface of the implantable artificial bone material including the calcium-based material can be removed by washing with a solution for washing. In a preferred embodiment of the method of production for the artificial bone material having controlled calcium ion elution of the present invention, includes subjecting to a washing treatment before treated with the surface-treating agent. In the step of washing, elimination of calcium ion includes not only removing calcium ions by diffusing the calcium ions in a solution for washing but reacting calcium ions with a component in the solution for washing to form a salt that remains on the surface of the implantable artificial bone material. Examples of such solution for washing include pure water, distilled water, a pH buffer solution, a chelating agent solution, a capping agent solution, and a coupling agent solution. In the step of washing, for washing the implantable artificial bone material, immersion washing, washing by shaking in liquid, running liquid washing, and the like can be used.

In the immersion washing, the steps of immersing the implantable artificial bone material in a solution for elimination, allowing it to stand for a given time, taking it out from the solution, and once again immersing it in a new solution for elimination and allowing it to stand, are repeated. Considering the steps of immersing the implantable artificial bone material in a solution for elimination, allowing it to stand for a given time, and taking it out from the solution as one cycle, the number of repeating is preferably 1 to 50 cycles, more preferably 2 to 30 cycles, and even more preferably 4 to 15 cycles. The immersion time of immersing the implantable artificial bone material in a solution for washing is preferably 1 second to 1 hour, and more preferably 10 seconds to 30 minutes. In cases of repeating immersing and taking out, the immersion time may be constant, but it is preferably gradually extended. The volume of the solution for washing with regard to the total volume of implantable artificial bone material to be immersed in the solution for washing is 2 to 50 times; however, the volume of the solution for washing may also be over 50 times. The volume of the solution for washing can be appropriately modified by those skilled in the art.

In the washing by shaking in liquid, the implantable artificial bone material is shaken in a solution for washing. For washing by shaking, any publicly known shaker can be used. Examples of methods of shaking include horizontal shaking, vertical shaking, swirl shaking, and rotation shaking and the like. The horizontal shaking is a back-and-forth motion in one direction on a horizontal plane. One back-and-forth motion is one cycle. In the horizontal shaking, the rate of shaking is preferably 1 to 50 cycle(s)/min, more preferably 5 to 30 cycle(s)/min, and even more preferably 10 to 20 cycle(s)/min. The vertical shaking is a seesaw motion. For example, a vertical shaker has a board for mounting a shaking vessel, in which the board has a supporting point in the center, and when the both ends of the board move up and down, one cycle of the vertical shaking includes the state where the board is at a horizontal attitude, one end moving upwards or downwards, and subsequently moving to the opposite direction and returning back to the horizontal attitude. In the vertical shaking, the rate of shaking is preferably 1 to 50 cycle(s)/min, more preferably 5 to 30 cycle (s)/min, and even more preferably 10 to 20 cycle(s)/min. The angle of the seesaw motion is, based on the horizontal position of a culture vessel at 0 degree, is preferably ±1 to 45 degrees, more preferably ±5 to 40 degrees, and even more preferably ±10 to 30 degrees. The swirl shaking is a gyrating motion in one direction on a horizontal plane. One cycle of the swirl shaking is one roll. In the swirl shaking, the rate of shaking is preferably 1 to 50 cycle(s)/min, more preferably 10 to 40 cycle(s)/min, and even more preferably 15 to 30 cycle(s)/min. The rotation shaking can be performed in a publicly known vessel for rotation shaking such as a cylindrical vessel using a publicly known apparatus. In the rotation shaking, the rate of rotation is 1 to 30 round(s)/min, preferably 5 to 25 round(s)/min, and more preferably 10 to 20 round(s)/min. The washing by such shaking allows calcium ions on the surface of the implantable artificial bone material to be easily dispersed in the solution for elimination, thereby allowing efficient removal of calcium ions. Shaking with the above-described rates enables the solution for elimination present at the interface with the implantable artificial bone material to circulate at a suitable rate to react with calcium ions on the surface of the implantable artificial bone material, thereby allowing efficiently calcium ions removal.

In the running liquid washing, a solution for elimination is sprayed onto the implantable artificial bone material. In the running liquid washing, a velocity of jet is 5 to 300 m/sec. In general, for the running liquid washing, a higher velocity is preferred because it exhibits higher washing performance. However, in the present invention, the solution of elimination reacts with calcium ions to eliminate the calcium ions, and a fast velocity of jet cannot sufficiently remove calcium ions. The velocity of jet is thus preferably 10 to 50 m/sec, and more preferably 20 to 30 m/sec. Use of such a velocity allows effective removal of calcium ions. The volume of jet and the time of running liquid washing can be appropriately adjusted. Preferable conditions are such that components that effuse as calcium ions are removed from the artificial bone material having controlled calcium ion elution by washing treatment so that an amount of calcium ion elution from the washed artificial bone material is 50% or less to that from the unwashed artificial bone material in a tissue around the implanted site of the artificial bone material under implanted conditions.

Solution of Dicarboxylic Acids

As described above, the implantable artificial bone material is preferably washed. The implantable artificial bone material is preferably permeated with succinic acid before or after washing. Succinic acid is thought to cause substitution of a phosphate ion of octacalcium phosphate (OCP) to a succinate ion when contacted with OCP (Hideki Monma and Masaru Goto, "Succinate-complexed Octacalcium Phosphate" Bull. Chem. Soc. Jpn., 56, pp. 3843-3844 (1983)). Permeation with succinic acid thus causes substitution of a phosphate ion to a succinate ion, thereby strongly fixing the calcium ion. Accordingly, the implantable artificial bone material permeated with succinic acid is thought to prevent calcium ion elution when the material is implanted in the body. Moreover, as shown in the Examples below, an artificial bone material having controlled calcium ion elution produced through these steps could prevent calcium elution from the artificial bone material and facilitate cell growth.

The method of the production of the present invention preferably further comprises a step of permeating the artificial bone material including the calcium-based material with the surface-treating agent.

Surface-Treating Agents

The surface-treating agent permeates onto/into the implantable artificial bone material by application or immersion. The term "permeated" refers to a state where the surface-treating agent is contained on the surface or contained internally in the implantable artificial bone material. The surface-treating agent is anyone or a mixture of anymore than one of an acidic solution, a chelating agent, a capping agent, and a coupling agent. The surface-treating agent of the present invention may be mixed with ingredients of the implantable artificial bone material or permeated into the implantable artificial bone material, by being dissolved in a publicly known solution capable of dissolving the surface-treating agent. For the solution to dissolve the surface-treating agent, any publicly known solution can be used if it can dissolve the surface-treating agent. Preferably water, saline, and alcohols and such are used. The concentration of the surface-treating agent is not specifically limited as long as the surface-treating agent is allowed to dissolve. However, at higher concentration, the surface-treating agent becomes viscous and more difficult to be permeated into the implantable artificial bone material under atmospheric pressure. Therefore, the surface-treating agent is preferably permeated under reduced or increased pressure. Under reduced or increased pressure, the permeation of surface-treating agent solution having high viscosity (high concentration) is more rapidly done than that of under atmospheric pressure. Conditions for immersing the implantable artificial bone material in the surface-treating agent solution to permeate the surface-treating agent into the implantable artificial bone material under reduced or increased pressure can be appropriately selected according to properties of the surface-treating agent solution and the implantable artificial bone material by those skilled in the art. In the present invention, different two or more surface-treating agents may be used in combination. The combination ratio of those surface-treating agents is not specifically limited. The combination ratio may be equal, or may be appropriately adjusted by those skilled in the art according to the properties of the surface-treating agents being used. Use of combined surface-treating agents allows prevention of calcium ion elution more effectively than using a surface-treating agent alone.

A higher weight of the surface-treating agent contained in the implantable artificial bone of the present invention results in insufficient strength for implantable artificial bone, and when it is too low it disables control of calcium elution, which is unfavorable. In the present invention, the weight ratio of the implantable artificial bone material to the surface-treating agent is $1\times10^2:1$ to $1\times10^5:1$, preferably $1.5\times10^2:1$ to $1\times10^4:1$, and more preferably $2\times10^2:1$ to $1\times10^3:1$. The artificial bone material containing the surface-treating agent at a weight ratio within such range has sufficient strength and exhibits controlled calcium ion elution.

The artificial bone material having controlled calcium ion elution of the present invention include those that the amount of calcium ion elution from the implantable artificial bone material is suppressed by 25 to 100%, preferably 50% or more, more preferably 70% or more, even more preferably 85% or more, as compared to the implantable artificial bone material which does not contain the surface-treating agent. By providing such ranges, calcium ion elution is suppressed and therefore allows prevention of the induction of inflammatory responses and cytotoxicity in a tissue adjacent to the implanted site, and thus, the artificial bone material having controlled calcium ion elution that can be favorably used is provided. In the artificial bone material having controlled calcium ion elution of the present invention, those that an amount of calcium ion elution is controlled in a tissue adjacent to the implanted site of the artificial bone material under implanted conditions, as compared to that from the unwashed artificial bone material as described above are preferred.

Acidic Solutions

The acidic solution of the present invention includes a solution which is one or a mixture of one or more selected from the group consisting of alginic acid, oxalic acid, lactic acid, terephthalic acid, phytic acid, and aluminic acid. Among these, the solution preferably contains either or both alginic acid and lactic acid. For dissolving these acidic substances, any publicly known solution can be used if it can dissolve these acidic substances and maintain the solution being acidic. Examples of the solution include water, saline, and alcohols. In general, a substance in a biomaterial applied to the body is selected from neutral substances according to pH in the body, if the substance remains in the biomaterial after applied to the body. Because acidic and alkali substances have a risk to harm cells in the body. In spite of this, in the present invention, use of acidic solution is preferred. The acidic solution reacts with calcium ions to form an insoluble matter. Use of the acidic solution allows to effectively prevent calcium ion elution from the carrier.

Chelating Agents

Examples of chelating agent include one or a mixture of more than one selected from the group consisting of, gluconic acid, chain polyphosphoric acid, aspartic acid, ethylenediaminetetraacetic acid (EDTA), phenanthroline, metaphosphoric acid, citric acid, malic acid, nitrilotriacetic acid (NTA), methylglycinediacetic acid, 1,2-cyclohexanediaminetetraacetic acid, diethylenetriamineacetic acid, diethylenetriaminepentaacetic acid (DTPA), 2-hydroxyethylethylenediaminetriacetic acid (HEDTA), triethylenetetraminehexaacetic acid (TTHA), 2-hydroxyethyliminodiacetic acid (HIDA), dicarboxymethylglutamic acid tetrasodium salt (GLDA), bis(2-hydroxyethyl)glycine (DHEG), dimethylglyoxime, dithizone, oxine, and acetylacetone, or pharmaceutically acceptable salts thereof. Among these, desirably used are one or a mixture of more than one selected from the group consisting of gluconic acid, chain polyphosphoric acid, aspartic acid, ethylenediaminetetraacetic acid (EDTA), metaphosphoric acid, citric acid, malic acid, nitrilotriacetic acid, and methylglycinediacetic acid. As described in the Examples below, those that contain gluconic acid is preferred. When permeating the chelating agent into the implantable artificial bone material under atmospheric pressure, the concentration of the chelating agent in the solution is 0.1 to 40% by weight, optionally 1 to 10% by weight, and further optionally 5 to 15% by weight. When permeating under reduced or increased pressure, the concentration may be more than 40% by weight as long as the chelating agent is allowed to dissolve. Conditions of reduced or increased pressure can be appropriately adjusted by those skilled in the art according to the materials of the carrier and the viscosity of the chelating agent solution and the like.

Capping Agents

The capping agent of the present invention preferably contains any one or more of amino acids, peptides, polysaccharides, disaccharides, lectin, proteoglycan, glycoproteins, and glycolipids.

Examples of the amino acid contained in the capping agent include any one or more of: amino acids selected from the group consisting of "alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine"; derivatives thereof, or pharmaceutically acceptable salts thereof. The amino acid is preferably of naturally occurring L-form. When permeating under atmospheric pressure, the concentration of the amino acid in the solution is preferably 0.01 to 10 mol/L, more preferably 0.05 to 5 mol/L, and even more preferably 0.1 to 2 mol/L. When permeating under reduced or increased pressure, the concentration may be more than 10 mol/L as long as the amino acid is allowed to dissolve. Conditions of reduced or increased pressure can be appropriately adjusted by those skilled in the art according to the materials of the carrier and the viscosity of the solution of the capping agent and the like.

Examples of the peptide contained in the capping agent include any one or more of dipeptides, tripeptides, tetrapeptides, pentapeptides or pharmaceutically acceptable salts thereof, in which the peptides are composed of any combination of amino acids selected from the group consisting of "alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine". Among these peptides, preferred are di- and tripeptides having a short peptide chain, because they allow the capping agent to rapidly permeate into the implantable artificial bone material. When permeating under atmospheric pressure, the concentration of the peptide in the solution is preferably 0.01 to 10 mol/L, more preferably 0.05 to 5 mol/L, and even more preferably 0.1 to 2 mol/L. When permeating under reduced or increased pressure, the concentration may be more than 10 mol/L as long as the peptide is allowed to dissolve. Conditions of reduced or increased pressure can be appropriately adjusted by those skilled in the art according to materials of the carrier and the viscosity of the solution of the capping agent and the like.

Examples of the polysaccharide contained in the capping agent include any one or more of pullulan, guar gum, λ carrageenan, tragacanth gum, pectin, mannan, dextran, maltodextrin, glucomannan, amylose, amylopectin, agarose, Tamarind seed gum, carrageenan, gellan gum, carboxy methyl cellulose, xanthan gum, karaya gum, gum arabic, gum ghatti, arabinogalactan, and curdlan, or acids salts thereof (e.g., a sulfate). Among them, preferred are pullulan, dextran, and maltodextran, and the more preferred is dextran. When permeating under atmospheric pressure, the concentration of the polysaccharide in the solution is preferably 1 to 40% by weight, more preferably 5 to 30% by weight, and even more preferably 15 to 25% by weight. When permeating under reduced or increased pressure, the concentration may be more than 40% by weight as long as the polysaccharide is allowed to dissolve. Conditions of reduced or increased pressure can be appropriately adjusted by those skilled in the art according to the materials of the carrier and the viscosity of the solution of the capping agent and the like.

Examples of the disaccharide contained in the capping agent include maltose, isomaltose, cellobiose, gentiobiose, nigerose, laminaribiose, kojibiose, suhorose, melibiose, lactose, turanose, sophorose, trehalose, isotrehalose, sucrose, lactose and isosaccharose. Among these disaccharides, preferred are trehalose, isotrehalose, maltose, isomaltose, cellobiose, or gentiobiose, and the more preferred is trehalose. As described in the Examples below, by containing trehalose calcium ion elution is effectively prevented. When permeating under atmospheric pressure, the concentration of the disaccharide in the solution is preferably 1 to 40% by weight, more preferably 5 to 30% by weight, and even more preferably 15 to 25% by weight. When permeating under reduced or increased pressure, the concentration may be more than 40% by weight as long as the polysaccharide is allowed to dissolve. Conditions of reduced or increased pressure can be appropriately adjusted by those skilled in the art according to the materials of the carrier and the viscosity of the solution of the capping agent and the like.

Examples of the glycoproteins contained in the capping agent include proteoglycans, mucin, and avidin. Among these, preferred is proteoglycans. One of proteoglycans is a complex of a mucopolysaccharide and a protein. Examples of mucopolysaccharide include hyaluronic acid, chondroitin sulfate, heparan sulfate, keratan sulfate, dermatan sulfate, and heparin. A concentration of the glycoprotein in the solution is 1 to 30% by weight, and preferably 15 to 25% by weight. Examples of the glycolipid contained in the capping agent include galactolipid, sulpholipid, sphingolipid (cerebroside, ganglioside), and glycophosphosphingolipid. The concentration of the glycolipid is 1 to 30% by weight and more preferably 10 to 20% by weight. Use of the solution having such a concentration allows to effectively perform the surface treatment.

Coupling Agents

Examples of the coupling agent contained in the surface-treating agent include aluminate, titanol, and silanol coupling agents. Among these coupling agents, preferred are the silanol coupling agents. The concentration of the coupling agent is 1 to 15% by weight, and preferably 5 to 10% by weight. In the present invention, the coupling agent preferably dissolves in a solution at a slightly acidic pH (pH 4.5 to 6.5). Use of the solution having such pH allows to enhance effects as surface-treating agents.

In a preferred embodiment of the first aspect of the present invention, the carrier having controlled calcium ion elution further contains a pharmaceutical agent. Examples of such pharmaceutical agent include cell membrane protective agents, anti-inflammatory agents, bone regenerative agents, and growth factors and the like.

Cell Membrane Protective Agents

Examples of the cell membrane protective agent of the present invention include polysaccharides, disaccharides, glycoproteins, glycolipids, and fatty acids. Preferred are disaccharides including maltose, isomaltose, cellobiose, gentiobiose, nigerose, laminaribiose, kojibiose, suhorose, melibiose, lactose, turanose, sophorose, trehalose, isotrehalose, sucrose, lactose and isosaccharose. More preferred are sucrose, lactose, trehalose, and maltose, and even more preferred are trehalose and sucrose.

Anti-Inflammatory Agents

Examples of the anti-inflammatory agent of the present invention include statins, steroids, and non-steroidal agents. Examples of statins include rosuvastatin, pitivastatin, simvastatin, pravastatin, cerivastatin, mevastatin, velostatin, fluvastatin, lovastatin, fluindostatin, and atorvastatin and such. Statins also have cell membrane protective effects, and the carrier having controlled calcium ion elution containing the statin is suitably applied to the body.

Examples of steroids include dexamethasone, triamcinolone acetonide, beclomethasone propionate, hydrocortisone succinate, methylprednisolone succinate, dexamethasone acetate, hydrocortisone acetate, prednisolone acetate, dexamethasone metasulfobenzoate, triamcinolone diacetate, prednisolone butylacetate, dexamethasone phosphate, hydrocortisone phosphate, prednisolone phosphate, betamethasone phosphate, prednisolone succinate, cortisone acetate, paramethasone acetate, methylprednisolone acetate, triamcinolone, hydrocortisone, prednisolone, betamethasone, prednisolone valerate acetate, diflucortolone valerate, dexamethasone valerate, betamethasone valerate, difluprednate acetate, diflorasone acetate, difluprednate, betamethasone dipropionate, flumethasone pivalate, fluocinonide, fluocinolone acetonide, alclometasone propionate, beclomethasone propionate, clobetasone butyrate, hydrocortisone butyrate, hydrocortisone butyrate propionate, fludrocortisone acetate, dexamethasone palmitate, and methylprednisolone.

Examples of non-steroidal agents include bufexamac, ibuprofen piconol, suprofen, ufenamate, indomethacin, piroxicam, ampiroxicam, meloxicam, lornoxicam, bendazac, ketoprofen, ibuprofen, flurbiprofen, naproxen, loxoprofen, alminoprofen, felbinac, diclofenac sodium, sulindac, flufenamic acid, mefenamic acid, tolfenamic acid, glycyrrhetinic acid and salts thereof, glycyrrhizic acid and salts thereof, glycol salicylate, and methyl salicylate.

Bone Regenerative Agents

Examples of bone regenerative agents include any one or a mixture of any more than one of calmodulin, actinomycin D, cyclosporine A, glucosamine sulfate, glucosamine hydrochloride, bone marrow extract, calcium phosphate, lactic acid/glycolic acid/ε-caprolactone copolymer, platelet-rich plasma, and human bone marrow-derived mesenchymal cell. These agents can be obtained by publicly known methods.

Growth Factors

A growth factor functions as a regulating factor of cellular proliferation, differentiation, in the process from initial development through maintaining individual life to aging in a multicellular organism life. Specific examples of the growth factor include such as, epidermal growth factor (EGF), insulin-like growth factor (IGF), transforming growth factor (TGF), vascular endothelial growth factor (VEGF), hepatocyte growth factor (HGF), platelet-derived growth factor (PDGF), embryonic smooth mascule myosin heavy chain (SMemb), bone morphogenetic protein (BMP), granulocyte colony-stimulating factor (G-CSF), erythropoietin (EPO), thrombopoietin (TPO), and basic fibroblast growth factor (bFGF). The carrier having controlled calcium ion elution containing the growth factor can facilitate cellular proliferation or the like in the affected site to which the carrier is applied, resulting in enhanced therapeutic effects. These growth factors can be obtained by publicly known methods, and one of or a mixture of more than one of them may be contained. In cases of applying the carrier having controlled calcium ion elution to a bone defect site or the like, the carrier preferably contains particularly a bone growth factor among these growth factors.

Bone Growth Factors

A bone growth factor is one of growth factors as described above, which is involved in bone growth and can be produced in the body. Examples of the bone growth factor include such as, epidermal growth factor (EGF), transforming growth factor β(TGF-β), insulin-like growth factor (IGF), vascular endothelial growth factor (VEGF), hepatocyte growth factor (HGF), platelet-derived growth factor (PDGF), embryonic smooth mascule myosin heavy chain (SMemb), and bone morphogenetic protein (EMP). These bone growth factors can be obtained by publicly known methods, and one of or a mixture of more than one of them may be used as a bone growth agent. As described in the Examples below, the carrier of the present invention can prevent calcium ion elution from the calcium-based material which is a component of the implantable artificial bone material in the carrier, and thus, can prevent induction of inflammatory responses, cytotoxicity, and the like at the implanted site. Bone growth factor and the like contained in the carrier of the present invention thus can effectively enhance therapeutic effects.

The present invention also relates to a method of producing an artificial bone material having controlled calcium ion elution. The method of production of the present invention comprises a step of washing an artificial bone material including a calcium-based material. The step of washing removes calcium ions that will leave from the surface of the artificial bone material when implanted in the body, thereby allowing to produce an artificial bone material having controlled calcium ion elution that can prevent induction of inflammatory responses and cytotoxicity elicited by the calcium ion in a tissue adjacent to the implanted site of the artificial bone material. In the method of production of the present invention, the step of washing uses pure water, a pH buffer solution, a chelating agent solution, a capping agent solution, or a coupling agent solution for washing. For the chelating agent, the capping agent, and the coupling agent, those described above can be used. In the present invention, pure water includes purified water, ultrapure water, and sterile water, as well as distilled water. Publicly known water used in production of artificial material may also be used.

pH Buffer Solution

In the process of the production of the present invention, any publicly known pH buffer solution can be used. Examples of the pH buffer solution include phosphate buffer saline (PBS), glycine-HCl buffer solution, citric acid-sodium citrate buffer solution, acetic acid-sodium acetate buffer solution, sodium succinate-NaOH buffer solution, sodium cacodylate-HCl buffer solution, sodium malate-NaOH buffer solution, Tris-malic acid buffer solution, MES-NaOH buffer solution, PIPES-NaOH buffer solution, MOPS-NaOH buffer solution, imidazole-HCl buffer solution, phosphate buffer solution, TES-NaOH buffer solution, HEPES-NaOH buffer solution, tricine-HCl buffer solution, Tris-HCl buffer solution, EPPS-NaOH buffer solution, glycylglycine-NaOH buffer solution, TAPS-NaOH buffer solution, boric acid-NaOH buffer solution, glycine-NaOH buffer solution, sodium carbonate-sodium hydrogen carbonate buffer solution, and sodium carbonate-NaOH buffer solution. These buffer solutions may be prepared according to publicly known methods. A concentration thereof in use may also be appropriately adjusted by those skilled in the art. Among these buffer solutions, preferred are those having a pH range within an acidic region in use. In general, for washing a substance to be applied to the body, a buffer solution having a pH range close to physiological conditions (pH 7 to 8) is used. However, in the present invention, preferred is a buffer solution having a pH range in use within an acidic region (pH 2 to 7). Among the buffer solutions described above, those having an acidic pH range are glycine-HCl buffer solution, citric acid-sodium citrate buffer solution, acetic acid-sodium acetate buffer solution, sodium succinate-NaOH buffer solution, sodium cacodylate-HCl buffer solution, sodium malate-NaOH buffer solution, Tris-malic acid buffer solution, and MES-NaOH buffer solution. Use of the buffer solution having an acidic pH range can effectively remove calcium ions.

The present invention also relates to a method of producing an artificial bone material having controlled calcium ion elution, including a step of washing an implantable artificial bone material with a gluconic acid solution and a step of permeating the washed implantable artificial bone material with a gluconic acid solution. The concentration of the gluconic acid solution in the step of washing is 0.1% to 20% by weight, preferably 0.2% to 10% by weight, and even more preferably 0.5% to 5% by weight. The concentration of the gluconic acid solution used in the step of permeating is 0.1% to 20% by weight, preferably 0.5% to 15% by weight, and even more preferably 2% to 10% by weight. For dissolving such gluconic acids, any publicly known solution can be appropriately used, including water and ethanol. In the steps of washing and permeating, the following processes as described below may be appropriately used.

According to the process of the production, an artificial bone material having controlled calcium ion elution can be produced in which an amount of calcium ion elution is suppressed by 25 to 100% of that from an implantable artificial bone material produced by a process other than the present invention. To achieve intended effects of preventing calcium ion elution, the step of washing or the step of permeating described below is appropriately adjusted and performed. The rate of calcium ion elution suppression is preferably 50% or more, more preferably 70% or more, and even more preferably 85% or more. The process of production of the present invention will be described in details below. However, the present invention is not limited by the following examples, and may be appropriately modified by those skilled in the art.

Permeation Step

The step of permeating the implantable artificial bone material with the surface-treating agent is conducted by applying the surface-treating agent to the implantable artificial bone material or immersing the implantable artificial bone material into a solution of the surface-treating agent. For absorption or application of the surface-treating agent, the method to be used is not particularly limited as long as the implantable artificial bone material is impregnated or applied with the surface-treating agent. In the process of the production of the implantable artificial bone material, the surface-treating agent may be mixed with the ingredients. Examples of methods for surface-treating agent permeation include immersion, spraying, and spin-coating. More specifically, the immersion is conducted by immersing the implantable artificial bone material in a solution of the surface-treating agent and keeping still in the solution for 1 to 6 hours at room temperature and atmospheric pressure to impregnate with the surface-treating agent. The step of impregnating with the surface-treating agent may be performed under reduced or increased pressure. The step performed under reduced or increased pressure allows the surface-treating agent permeating the implantable artificial bone material in a shorter time than that of under atmospheric pressure. Conditions under reduced or increased pressure can be appropriately adjusted by those skilled in the art according to the implantable artificial bone material and the solution of the surface-treating agent. For applying the surface-treating agent, the following methods also may be used, including spraying and spin-coating. The implantable artificial bone material permeated with the surface-treating agent may be sterilized.

Step of Drying the Surface-Treating Agents

In a preferred embodiment of the present invention, the method of production further comprises a step of drying the implantable artificial bone material permeated with the surface-treating agent. After the implantable artificial bone material permeated with the surface-treating agent is dried, a step of introducing a pharmaceutical agent is performed to allow the implantable artificial bone material to uniformly contain the pharmaceutical agent. The step of drying may be appropriately adjusted according to properties of the surface-treating agent and the like. For example, the step is performed by placing and keeping still in a dryer at 30 to 200° C. The drying time is 2 to 60 minutes, or may be longer than 60 minutes. To reduce the drying time, the implantable artificial bone material may be allowed to stand under blowing and for example, includes the wind speed of 0.1 to 5 m/sec. However, the wind speed too fast or too slow results in unevenness. A slower speed takes longer time for drying and thus, reduces production efficiency. The wind speed is thus preferably 0.2 to 3 m/sec, and more preferably 0.5 to 1.5 m/sec.

The present invention will be illustrated by reference with the following Examples, but is not limited by these Examples. The present invention includes appropriate modifications and variations within the range clearly recognized by those skilled in the art.

Production Example 1

Production of an implantable artificial bone material Using a-TCP (Taihei Chemical Industrial Co., Ltd.) as a main ingredient, an implantable artificial bone material was produced with Z printer 406 (Z corporation). The produced implantable artificial bone material was immersed in a curing solution. The curing solution used was an aqueous 0.2 mol/L succinic acid solution (pH 6). Then, the immersed tetrapod carrier having controlled calcium ion elution was washed twice with Otsuka distilled Water, and dried for 12 hours under reduced pressure in a vacuum low temperature dryer (Yamato Scientific Co., Ltd.).

Example 1

Study for Increased Calcium Ion and Cytotoxicity

Effects of Trehalose Treated Artificial Bone Material on Preventing Calcium Ion Elution from the Same Artificial bone materials untreated and treated with trehalose were respectively co-cultured with a mouse osteoblastic-like cell MC3T3-E1 and measured for cell growth to evaluate cytotoxicity due to calcium ion elution. For a culture medium, Dulbecco's Modified Eagle Medium (D-MEM) containing 10% fetal bovine serum (FBS) and 1% penicillin-streptomycin was used. Implantable artificial bone materials prepared as in Production Example 1 (untreated tetras) or those prepared therefrom by treating with (immersing in) a 4.5% trehalose solution (treated tetras) were respectively placed in wells of 96-well plate. For a control experiment, wells without an implantable artificial bone material (no tetras) were also prepared. To these wells, mouse osteoblastic-like cells, MC3T3-E1, were then plated at 2500 cells/well. Cells were incubated for 72 hours, and then Cell Counting Kit-8 (Dojindo Kagaku Kenkyusyo) was added to cause a color reaction. Then, the samples were measured for absorbance (450 nm) with a microplate reader to determine cell growth. The results are shown in FIG. 1.

FIG. 1 shows affects of calcium ions eluted from a carrier on cell growth. The vertical axis of FIG. 1 is a value of absorbance indicating cell growth. The larger value of absorbance means the better cell growth. In FIG. 1, "tetra" refers to the carrier in the form of tetrapod. The results show that wells containing carriers untreated with trehalose (untreated tetras) had lower absorbance than wells without tetras or containing two tetras. This means that the number of cells in a well containing untreated tetras was less than that of those in wells without tetras or containing treated tetras. From the results, it is shown that the implantable artificial bone material rather suppresses cell growth or has toxicity. In contrast, the number of cells in a well containing two treated tetras is more than that of those in wells without tetras or containing untreated tetras. The results suggest that calcium ion elution from the carrier was probably prevented by covering the surface of the implantable artificial bone material with trehalose.

Example 2

Study for Chelating Effects of Gluconic Acid

Figure 2:
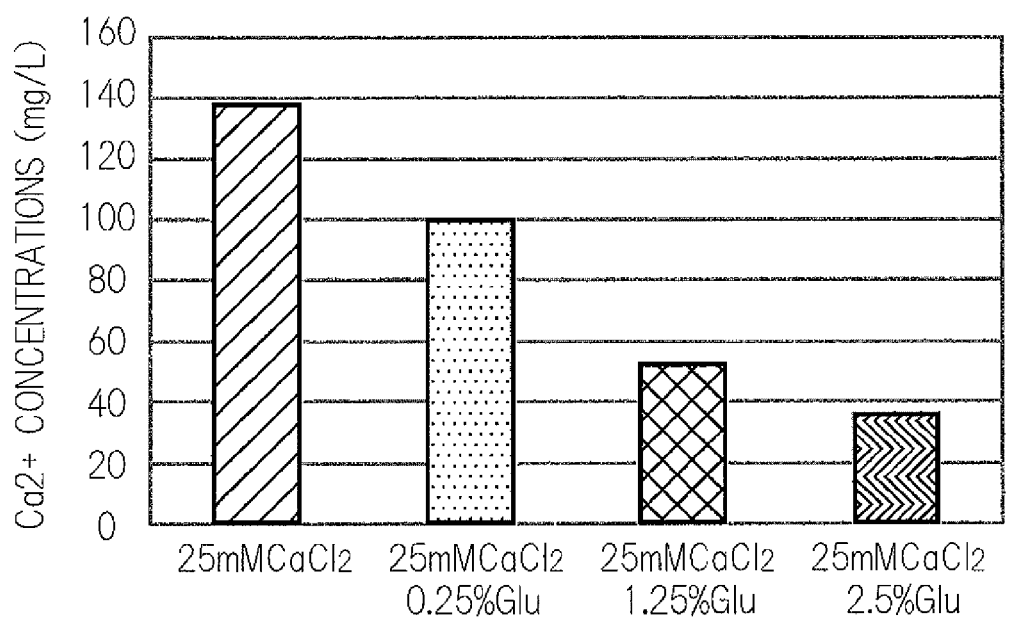
FIG. 2 is a graph, in place of a drawing, showing gluconic acid chelating calcium ion.

To confirm chelating effects of gluconic acid on calcium ion, the concentration of calcium ion in the presence of gluconic acid was measured with a calcium ion electrode. The results are shown in FIG. 2. The vertical axis of FIG. 2 indicates the concentration of calcium ion ($Ca^{2+}$) (mg/L). Solutions of 0.25% to 25% gluconic acid (Glu) containing 2.5 mM $CaCl_2$ (pH 7.0) were prepared and measured for calcium ion concentrations, which the results showed that the higher the concentration of gluconic acid became, the concentration of calcium ion lowered. The results might be attributed to the gluconic acid chelating calcium ions.

Since gluconic acid chelates calcium ions leaving from the implantable artificial bone material and attaching to the surface and the like of the implantable artificial bone material, the washing treatment of the implantable artificial bone material with a gluconic acid solution can effectively remove calcium ions attached to the surface and the like of the implantable artificial bone material. Alternatively, the implantable artificial bone material is permeated with a gluconic acid solution to allow the gluconic acid solution to chelate the calcium ions leaving from the implantable artificial bone material, thereby preventing calcium ion elution from the implantable artificial bone material.

Example 3

Effects of Gluconic Acid on Prevention of Inflammatory Response Induction

An increased concentration of extracellular calcium ions activates an inflammatory response route through increase of intracellular calcium ion and/or a sensing mechanism of extracellular calcium ion. The present inventors studied whether induction of inflammatory responses due to increase of calcium ions can be prevented or not by chelating calcium ions. Solutions of 5 mM $CaCl_2$—0.384% gluconic acid and 7.5 mM $CaCl_2$—0.384% gluconic acid (referred to as $Ca^{2+}$ Gluc.Acid), the pH of which were adjusted to approximately 7 with NaOH, were prepared and allowed to stand for one hour at room temperature. Macrophage-like cells RAW267.4, which were labeled with 1 µCi [$^3$H] arachidonic acid one day before, were treated with respective CaCl2-gluconic acid solutions for one hour, and measured for the amount of released lipid mediator with a liquid scintillation counter. The results are shown in FIG. 3.

Figure 3A:
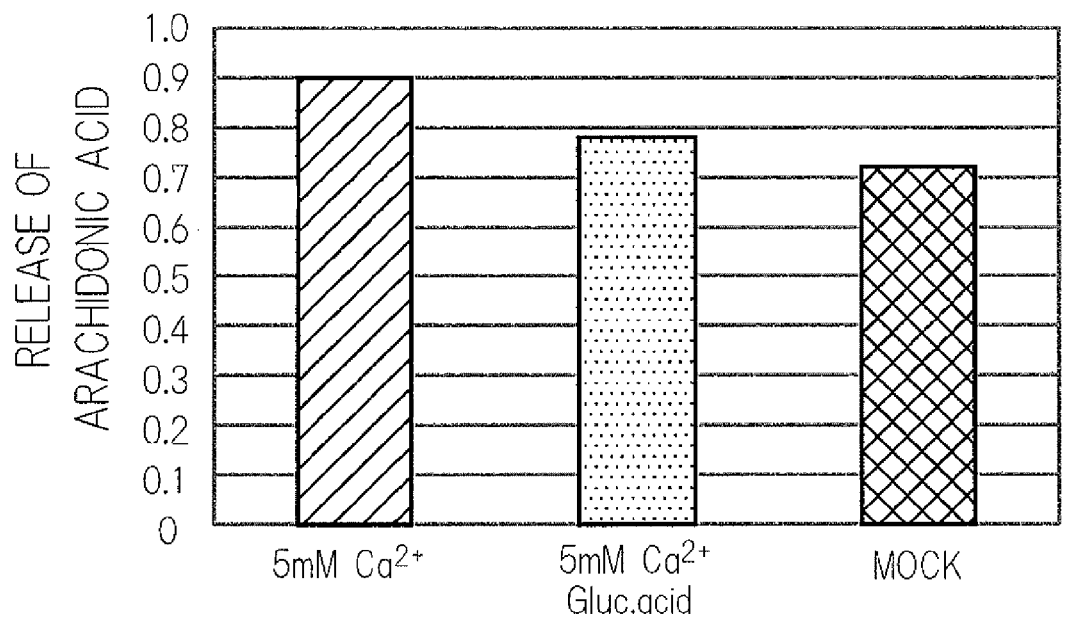
FIG. 3A is a graph in place of a drawing, showing gluconic acid preventing induction of inflammatory responses by 5 mM calcium hydrochloride.
Figure 3B:
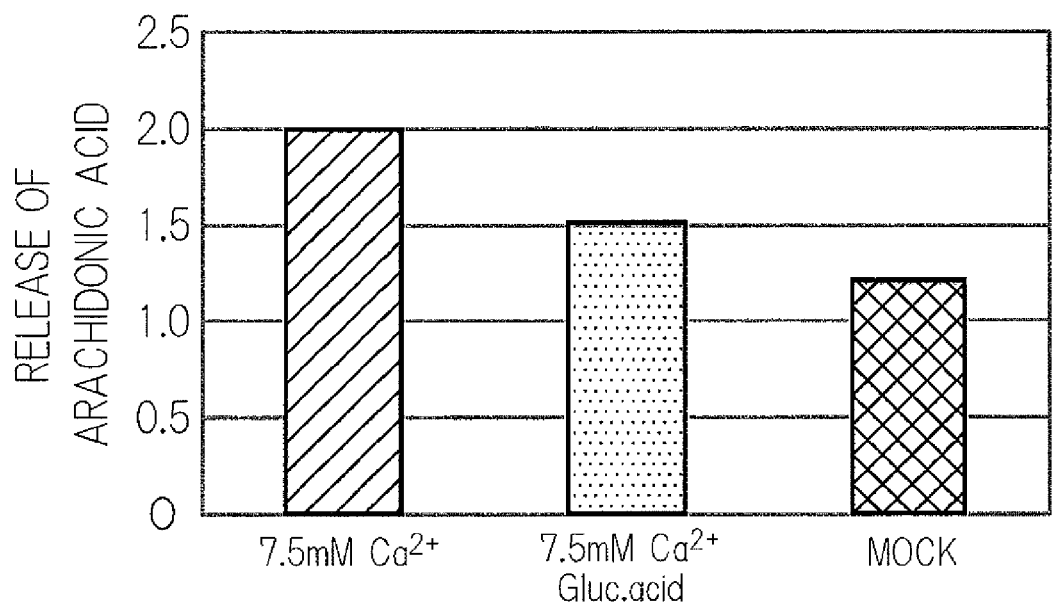
FIG. 3B is a graph, in place of a drawing, showing gluconic acid preventing induction of inflammatory responses by 7.5 mM calcium hydrochloride.

FIG. 3 is a graph, in place of a drawing, showing that gluconic acid prevents inflammatory responses induced by calcium ions. Each vertical axis of FIGS. 3A and 3B indicates release of arachidonic acid (rates of released [$^3$H] arachidonic acid). The higher value refers to more arachidonic acid being released, indicating an activation of arachidonate cascade, which is one of the major inflammatory responses. In FIG. 3, the "mock" refers to a sample without $CaCl_2$ or gluconic acid addition, which was prepared as a control. The results revealed that, compared with the mock, cells added with $CaCl_2$ released increased amount of lipid mediator and activated the arachidonate cascade which is one of the major inflammatory response routes, but in cells in the presence of gluconic acid arachidonate cascade activation was prevented. It is believed that gluconic acid chelates calcium ions, reducing the concentration of free calcium ion, thereby preventing the activation of the arachidonate cascade. It thus can be said that use of gluconic acid can prevent inflammatory responses due to calcium ions. Calcium ions leaving from the implantable artificial bone material and attaching to the surface and the like of the implantable artificial bone material can be removed by the washing treatment of the implantable artificial bone material with a gluconic acid solution. Alternatively, calcium ions in the implantable artificial bone material can be prevented from leaving therefrom by the permeating the implantable artificial bone material with the gluconic acid solution. Accordingly, washing or permeating an implantable artificial bone material with gluconic acid solution thus can provide effects to prevent inflammatory responses at the site where the implantable artificial bone was implanted.

INDUSTRIAL APPLICABILITY

The carrier having controlled calcium ion elution of the present invention is suitably used in the field of medicine such as applying to a bone defect site.

The invention claimed is:
1. A method for producing sintered artificial bone material having controlled calcium ion elution, comprising a step of washing a sintered artificial bone material which comprises a calcium-based material, with a chelating agent to remove the calcium ion that will leave from a surface of the artificial bone material when the artificial bone material is implanted in a body,
   wherein the sintered artificial bone material thereby produced has controlled calcium ion elution and thus prevents inflammatory responses and cytotoxicity excited by the calcium ion in a tissue adjacent to a site where the artificial bone material is implanted.
2. The method for producing an artificial bone material having controlled calcium ion elution according to claim 1, wherein the step of washing reduces the amount of calcium ion which would leave from the surface of the artificial bone material upon implantation in a body by 50% or more.

3. The method for producing an artificial bone material having controlled calcium ion elution according to claim 1, further comprising a step of permeating the washed artificial bone material with a surface-treating agent, wherein the surface-treating agent comprises any one or more species selected from a group consisting of a pH buffer, a chelating agent, a capping agent, and a coupling agent.

4. The method for producing an artificial bone material having controlled calcium ion elution according to claim 1, wherein the step of washing uses a gluconic acid solution as a chelating agent to wash the artificial bone material, and the method further comprises a step of permeating the washed implantable artificial bone material with gluconic acid.

5. The method for producing an artificial bone material having controlled calcium ion elution according to claim 1, wherein the artificial bone material comprising the calcium-controlled material is permeated with succinic acid,
the step of washing uses succinic acid as a chelating agent to wash the succinic acid permeated bone material, and
the method further comprises a step of permeating the washed implantable bone material with trehalose.

\* \* \* \* \*